(12) United States Patent
Lo

(10) Patent No.: US 11,020,479 B2
(45) Date of Patent: Jun. 1, 2021

(54) METHOD FOR PRODUCTION OF SOLID WATER PARTICLES FOR HOMEOPATHY

(71) Applicant: American Quantum Health Inc, Arcadia, CA (US)

(72) Inventor: Shui Yin Lo, Pasadena, CA (US)

(73) Assignee: American Quantum Health Inc, Arcadia, CA (US)

( * ) Notice: Subject to any disclaimer, the term of this patent is extended or adjusted under 35 U.S.C. 154(b) by 427 days.

(21) Appl. No.: 14/714,778

(22) Filed: May 18, 2015

(65) Prior Publication Data

US 2015/0335740 A1 Nov. 26, 2015

Related U.S. Application Data

(60) Provisional application No. 62/000,555, filed on May 20, 2014.

(51) Int. Cl.
*A61K 41/00* (2020.01)
*A61K 45/06* (2006.01)
*A61K 9/08* (2006.01)

(52) U.S. Cl.
CPC .......... *A61K 41/0004* (2013.01); *A61K 45/06* (2013.01); *A61K 9/08* (2013.01)

(58) Field of Classification Search
CPC ....... A61K 41/0004; A61K 45/06; A61K 9/08
See application file for complete search history.

(56) References Cited

U.S. PATENT DOCUMENTS

| 5,629,286 A * | 5/1997 | Brewitt | A61K 41/0004 |
| | | | 424/600 |
| 2010/0273896 A1 * | 10/2010 | Lo | A61K 8/02 |
| | | | 514/769 |

* cited by examiner

*Primary Examiner* — Robert S Cabral
(74) *Attorney, Agent, or Firm* — Elizabeth Yang

(57) ABSTRACT

A method for production of solid water particles for homeopathy uses principles of quantum physics to from a concentrated solid water particle solution. A homeopathic ingredient solution is diluted in purified water in an inert gas environment. The dilution occurs as infinitesimal doses, in which the solution is repetitively diluted in water past the point where few molecules from the solution remain. An electrical field is applied to align the water molecules for formation of a large clump of solid water particles. Alternating phases of ultrasonic vibrations break down the large clump into small clusters of solid water particles. The vibration is followed by periods of rest, whereby the small clusters grow into successively larger clumps by absorbing water molecules. The vibrations and resting are repeated in cycles until a desired concentration of solid water particles form in the solid water particle solution.

16 Claims, 6 Drawing Sheets

METHOD FOR PRODUCTION OF SOLID WATER PARTICLES FOR HOMEOPATHY

CROSS-REFERENCE TO RELATED APPLICATIONS

This Non-Provisional Patent Application claims priority from the Provisional Patent Application No. 62/000,555.

FIELD OF THE INVENTION

The present invention relates generally to a method for production of solid water particles for homeopathy. More so, a homeopathic method uses principles of quantum physics to produce a concentrated solid water particle solution through serial dilutions in a purified water and inert gas environment, and then apply an electrical field to the solution, and then disrupt the solution with sonic vibrations to break down the clumps of solid water particles into smaller clusters, which are then rested so they can grow into yet larger clumps of solid water particles until a desired concentration of solid water particle solution is achieved.

BACKGROUND OF THE INVENTION

Typically, homeopathy involves a method of treating disease by drugs, given in minute doses that would produce in a healthy person symptoms similar to those of the disease. Homeopathy's first law, "similia similibus curentur," or let likes be cured by likes. In other words, drugs which cause specific symptoms can be used to cure diseases which cause the same symptoms.

It is known that homeopathy also adheres to the law of infinitesimal doses, which states that when drugs are diluted in either water or alcohol, they actually increase in therapeutic potency. In many instances, serial dilutions of 1:100 repeated 6 or 30 times are used. Between each dilution the substance is violently shaken, which is thought to be necessary to activate the properties of the drug.

Generally, homeopathic medicines are well known, and in general. The homeopathic medicines were initially developed through the Hahnemanian process. The Hahnemanian process involves an active homeopathic ingredient that is dispersed in a carrier solution, generally, a solution of water, alcohol, or an alkaloid mixture. Where the carrier solution is a water, the water is normally purified prior to mixing. The active homeopathic ingredient of the medicine is mixed with the carrier solution in the appropriate proportion to achieve the desired concentration of the active homeopathic ingredient in the carrier solution.

Often, the homeopathic solution is not very effective. This can be because of a number of things:

1) The water is not clean enough. Since it relies on very small seed to start the dilution. The water must be the cleanest technologically.

2) The air under it is produced is not clean enough. There are dirt in the air. As the solution is produced, minute amount of dirt in the air will make the signal from the original seed smaller and smaller.

3) The air contains carbon dioxide. When purified water is produced with PH value equal to 7, as soon as it touches air, carbon dioxide dissolves in the water to become carbonic acid. The PH value reduces rapidly to 6, and gradually to 5.3.

It is known that water clusters, method of their manufacture as well as methods of their manufacture and use are known in the art. They are disclosed for example in Proceedings of First International Conference of the Physical, Chemical and Biological Properties of Stable Water Clusters, edited by B. Bonavita, S. Y. Lo, World Scientific 1997, and in U.S. Pat. Nos. 5,800,576; 5,997,590; U.S. patent application publication 2006/0110418, international patent application publication WO 2009/04912, U.S. patent application publication 2005/0270896, U.S. Pat. No. 6,487,994, U.S. patent application publication 2004/0025416.

Other proposals have involved homeopathic formulations and methods for producing. The problem with these devices is that they do not provide effective medical therapy due to the impure production.

Thus, an unaddressed need exists in the industry to address the aforementioned deficiencies and inadequacies. Even though the above cited methods for homeopathic medication meets some of the needs of the market, method for production of solid water particles through homeopathy uses principles of quantum physics to from a concentrated solid water particle solution is still desired.

SUMMARY OF THE INVENTION

The present invention is directed to a method for production of solid water particles for homeopathy.

The method for production of solid water particles through homeopathy uses principles of quantum physics to from a concentrated solid water particle solution. A homeopathic ingredient solution is diluted in purified water in an inert gas environment. The dilution occurs as infinitesimal doses, in which the solution is repetitively diluted in water past the point where few molecules from the solution remain. An electrical field and/or an electromagnetic field is applied to align the water molecules for formation of a large clump of solid water particles.

In some embodiments, alternating phases of ultrasonic vibrations disrupt, or break down, the large clump into small clusters of solid water particles. The vibration is followed by a predetermined duration of rest, whereby the small clusters grow into successively larger clumps by absorbing water molecules. In this manner, the clumps progressively increase in size, along with the concentration of solid water particles. The vibrations and resting are repeated in cycles until a desired concentration of solid water particle solution forms. Since solid state particles i.e., $PH_2O$ are formed, disrupted, and then allowed to grow again, the mechanisms of quantum physics are in effect with the present method.

Those skilled in the art will recognize that the method improves upon homeopathic remedy solutions, and is similar to the original production of homeopathic remedies, except that purified air and water are used, and no shaking during the dilution process is involved. Also, an electrical field aligns the water molecules for more efficient formation of solid water particles.

The method may include an initial Step of performing serial dilution of a homeopathic ingredient solution in purified water. The dilution is performed in air that is free of carbon dioxide, such as an inertia gas, such as argon or pure nitrogen gas. A Step comprises applying an electrical field to the homeopathic ingredient solution and the purified water. The electrical field aligns the water molecules, such that a large clump of solid water particles forms. The electrical field may include, without limitation, a direct current electrical field. In some embodiments, an electromagnetic field is also applied with the electrical field.

A Step comprises forming a solid water particle solution, the solid water particle solution comprising a large clump of solid water particles. A Step may include applying, in a water bath, an ultrasonic vibration to the solid water particle solution. Generally, cavitation in the solid water particle solution generates vigorous vibrations.

The method may then utilize a Step of disrupting the large clump of the solid water particles, wherein the disruption breaks the large clump into a small cluster of the solid water particles. During this Step, the small cluster generally absorbs surrounding water molecules, creating further growth of the small cluster. A Step comprises resting the small cluster for a predetermined duration, wherein the inactive period enables the small cluster to grow larger than the prior large clump of the solid water particle.

A Step further includes repeating the ultrasonic vibration Step and the resting Step until a predetermined concentration of solid water particles forms in the solid water particle solution. Those skilled in the art will recognize that a continuous cycle of sonic vibrations and rest allow for the maximum growth rate of clusters of solid water particles resulting in a solution with a higher concentration of solid water particles than can be achieved by just serial dilution alone. A final Step comprises administering the solid water particle solution for therapeutic relief. Myriad diseases and ailments may be addressed through this homeopathic medication.

One objective of the present invention is to provide a more effective homeopathic ingredient solution through homeopathy.

Another objective is to enhance homeopathy by improving the quality and quantity of solid water particles that are used for a homeopathic ingredient solution.

Another objective is to dilute a homeopathic ingredient solution in purified water, and in an environment of inert air that contains no carbon dioxide.

Another objective is to provide purified water within a range of 16-20 million ohms per centimeter quality.

Another objective is to form solid water particle solution more efficiently by exposing the water molecules to an electrical field and an electromagnetic field.

Yet another objective is to provide a method for producing clusters of solid water particles.

Yet another objective is to use the cluster of solid water particles with other methods for producing additional homeopathic ingredient solutions.

Yet another objective is to produce a therapeutic solid water particle solution with minimal expenses and with standard laboratory equipment.

Yet another objective is to produce a colloidal suspension of a second material, so that surrounding water molecules and stable water clusters will attach to thusly produced charge spots and new stable water clusters will grow while existing stable water clusters created by a first material will grow larger.

Yet another objective is to produce a solution of solid stable water molecules can be used as a fuel catalyst in the additional material which is a combustible fuel selected from the group consisting of gasoline, diesel, natural gas, jet fuel, heavy oil, and coal.

Yet another objective is to produce a solution of solid stable water clusters can be used with an additional material used in processing plants that produce petroleum derived products selected from the group consisting of oil refineries, power plants, and manufacturing facilities, to reduce coking.

Yet another objective is to produce a solution of solid stable water clusters can be introduced into the additional material which is a material used in a skin care product so as to produce the skin care product with the solid stable water clusters.

Yet another objective is to produce a solution of solid stable water clusters that can be also introduced into the additional material which is used for health purposes so as to produce a health product.

Other systems, devices, methods, features, and advantages will be or become apparent to one with skill in the art upon examination of the following drawings and detailed description. It is intended that all such additional systems, methods, features, and advantages be included within this description, be within the scope of the present disclosure, and be protected by the accompanying claims and drawings.

BRIEF DESCRIPTION OF THE DRAWINGS

The invention will now be described, by way of example, with reference to the accompanying drawings, in which:

FIG. 4A illustrates a large clump with ten dipoles, FIG. 4B illustrates two smaller clusters with five dipoles each shown in the middle, and FIG. 4C illustrates each small cluster picking up one new dipole to become two bigger clusters, each with six dipoles, in accordance with an embodiment of the present invention;

FIG. 5A illustrates ten dipole cluster breaking up into two different smaller clusters, each of which has five dipoles, and FIG. 5B illustrates the two smaller clusters picking up six dipoles, in accordance with an embodiment of the present invention; FIG. 6A illustrates a large ten dipole cluster breaking up another two different smaller clusters, and FIG. 6B illustrates two smaller clusters picking up ten new dipoles to form two big clusters of ten dipole each, in accordance with an embodiment of the present invention.

Like reference numerals refer to like parts throughout the various views of the drawings.

DETAILED DESCRIPTION OF THE INVENTION

Figure 1:
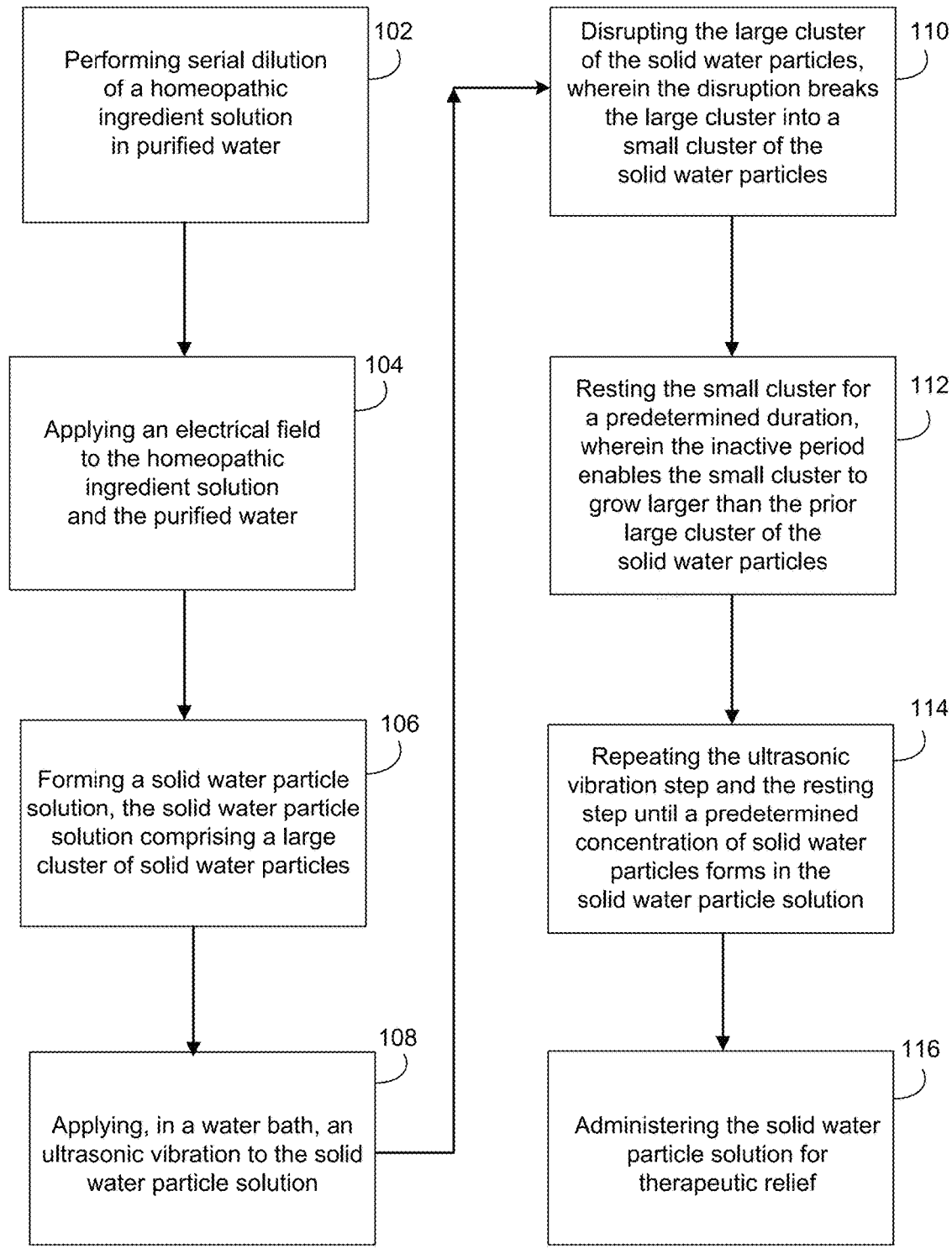
FIG. 1 illustrates a flowchart diagram of an exemplary method for production of solid water particles for homeopathy, in accordance with an embodiment of the present invention.
Figure 2:
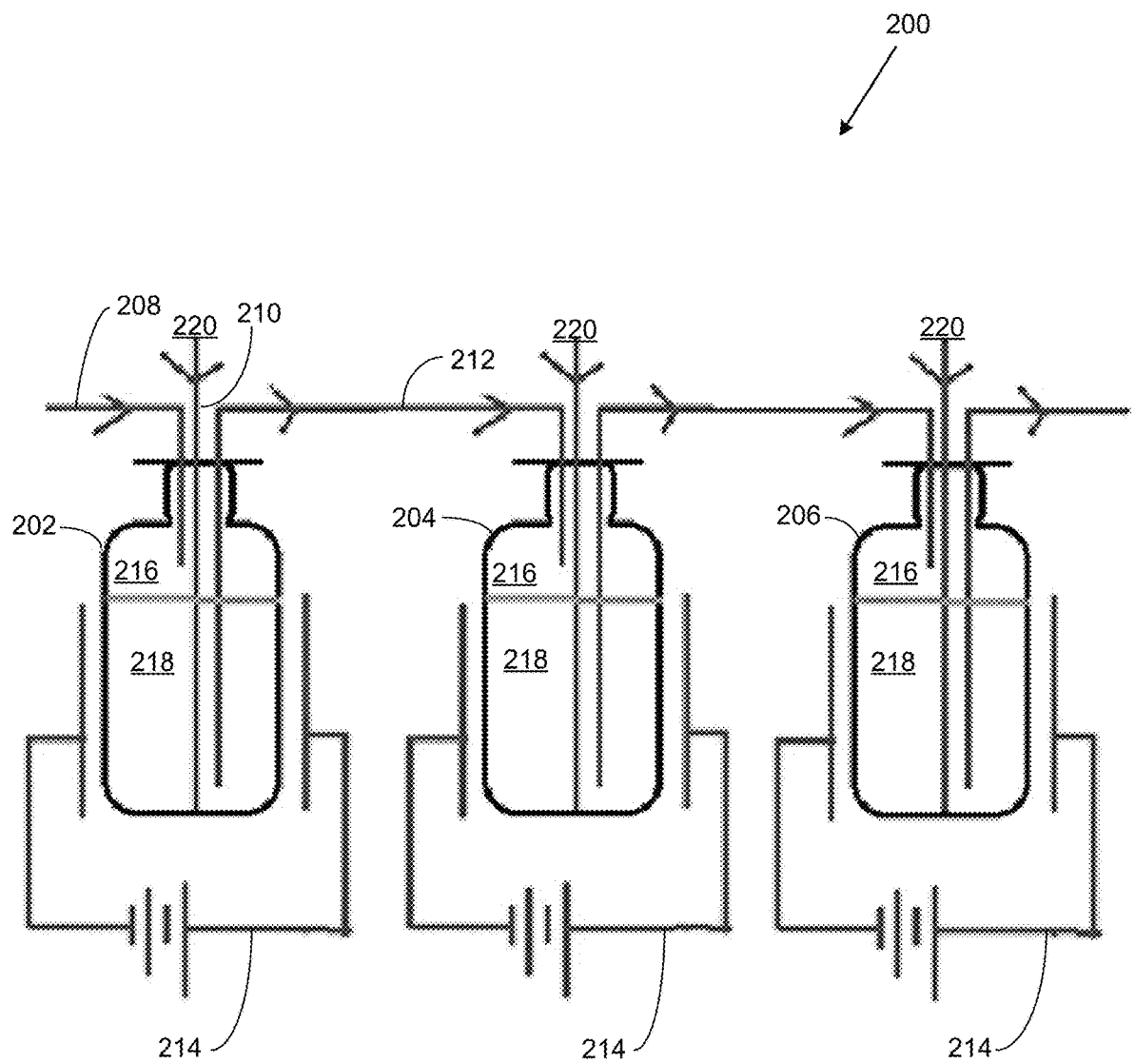
FIG. 2 illustrates an exemplary dilution system that performs serial dilutions of a homeopathic ingredient solution in purified water and an inert gas environment, in accordance with an embodiment of the present invention.

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "first," "second," "left," "rear," "right," "front," "vertical," "horizontal," and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

At the outset, it should be clearly understood that like reference numerals are intended to identify the same structural elements, portions, or surfaces consistently throughout the several drawing figures, as may be further described or explained by the entire written specification of which this detailed description is an integral part. The drawings are intended to be read together with the specification and are to be construed as a portion of the entire "written description" of this invention as required by 35 U.S.C. § 112.

In one embodiment of the present invention presented in FIGS. 1-6B, a method 100 for production of solid water particles through homeopathy is referenced. The method 100 for production of solid water particles through homeopathy, hereafter, "method 100", uses principles of quantum physics to produce a concentrated solid water particle solution 300 for more effective homeopathy. The method 100 progressively grows clumps of solid water particles in a homeopathic ingredient solution 218 and purified water 220 until large clumps of solid water particles form. The clumps produce a concentrated form of the solid water particle solution 300. The solid water particle solution 300 may then be administered to provide effective medical relief, as needed. The method 100 applies general principles of quantum mechanics and standard wet chemistry techniques known in the art.

Initially, a dilution system 200 performs serial dilutions of a homeopathic ingredient solution 218 and purified water 220 in an inert gas 216 environment. The dilution occurs as infinitesimal doses, in which the homeopathic ingredient solution 218 is repetitively diluted in the purified water 220 past the point where few molecules from the solution remain. Next, an electrical field and/or an electromagnetic field is applied to align the water molecules in the homeopathic ingredient solution 218. The alignment is possible because of the atomic structure of water. The alignment facilitates formation of a large clump 404 of solid water particles, whereby a concentrated solid water particle solution 300 forms.

In some embodiments, alternating phases of ultrasonic vibrations disrupt, or break down, the large clump 404 into a plurality of small clusters 406a, 40b containing the same solid water particles. The vibration is followed by a predetermined duration of rest for the solid water particle solution 300, whereby the small clusters 406a-b grow into successively larger clumps 404 by absorbing the remaining water molecules. In this manner, the clusters 406a-b progressively increase in size, along with the concentration of solid water particle solution 300. Thus, the vibrations and resting practiced in the method 100 are repeated in cycles until a desired concentration of solid water particle solution 300 forms. It is significant to note that, since solid state particles i.e., $PH_2O$ are formed, disrupted, and then allowed to grow again, the mechanisms of quantum physics are in effect with the present method 100.

In some embodiments, after the dilution is completed, an electrical field is applied to align the water molecules for formation of the large clump 404 of solid water particles. A circuitry 214, such as a battery, wire, or voltage may apply a direct current across the solid water particle solution 300 for this purpose. After the application of the electrical field, alternating phases of ultrasonic vibrations break down the large clump into a small cluster of solid water particles. The vibration is followed by a predetermined duration of rest, in which the small clusters 406a-b grow into a larger clumps 404 by absorbing water molecules. The clumps 404 progressively grow larger with every phase of vibration and rest. The vibrations and resting are repeated in cycles until a desired concentration of solid water particle solution 300 forms. Since solid state particles i.e., $PH_2O$ are formed, broken down, and then allowed to grow again, the mechanisms of quantum physics are in effect with the present method 100.

Those skilled in the art will recognize that the method 100 improves upon homeopathic remedy solutions, and is similar to the original production of homeopathic remedies, except that purified water 220 and inert gas 216 are used, and no shaking or agitation occurs during the dilution process. Also, an electrical field and/or electromagnetic field aligns the water molecules for more efficient formation of solid water particles.

As referenced in the flowchart diagram of FIG. 1, the method 100 may include an initial Step 102 of performing serial dilution of a homeopathic ingredient solution 218 in purified water 220 and in an environment of inert gas 216. Thus, the dilution occurs in an environment free of carbon dioxide, such as in pure nitrogen gas, pure argon, or any other pure inertia gas environment. Consequently, a sterile environment is created for dilution of the homeopathic ingredient solution 218. Also, highly purified water 220 is used for production of the homeopathic ingredient solution 218. The purified water 220 may be purified through distillation, filtering, ultraviolet light, or other means known in the art. In one possible embodiment, the purified water 220 has a resistivity of 18.2 Mohm/cm, and PH value of 7.

Those skilled in the art will recognize that an inert gas 216 is vital for maintaining the water at a desired pH and purity. For example, air contains carbon dioxide, while purified water 220 has a pH of 7. However, as soon as the carbon dioxide found in air dissolves in the purified water 220, the purified water 220 becomes carbonic acid, and the pH value reduces rapidly to 6, and gradually to 5.3. This lower pH inhibits formation of the desired homeopathic ingredient solution 218. Therefore, inert air must be used for dilution.

After multiple dilutions of the homeopathic ingredient solution 218, the percentage of ordinary matter in the homeopathic ingredient solution 218 is negligible and cannot be detected. This is known as the law of infinitesimal doses. In essence, the homeopathic ingredient solution 218 is diluted to the point to where it only water molecules, each of which consists of two hydrogen atoms and one oxygen atom. It is significant to note that a substance of a stable water cluster is the product for the method 100. The name for the water cluster is the aforementioned solid water particle.

In one exemplary dilution, a liter of solid particle water solution 300 with a concentration of one thousandth of one mole ($10^{-3}$ M) is prepared. As referenced in FIG. 2, a dilution assembly 200 is used to prepare the solid particle water solution 300. Initially, a homeopathic ingredient solution 218 is diluted with purified water 220 to achieve the solid particle water solution 300 with the desired concentration.

The homeopathic ingredient solution 218 may include, without limitation, a medical substance, a drug, a liquid, and a powder. In one exemplary dilution process, approximately 10 ml of the homeopathic ingredient solution 218 is sucked into a first bottle 202 through a first tube 208. Then, a second tube 210 sucks in 1 liter of purified water 220 into the first bottle 202. In this manner, the homeopathic ingredient solution 218 is diluted 100 times.

A second dilution occurs as approximately 10 ml of the diluted homeopathic ingredient solution 218 is sucked from the first bottle 202 to a second bottle 204 through a third tube 212. Approximately 1 liter of purified water 220 is then sucked into the second bottle 204 for dilution of 100 times. The same dilution procedure may be repeated until a desired concentration is achieved.

For example, 10 ml of the diluted homeopathic ingredient solution 218 in the second bottle 204 is sucked into a third bottle 206 through a third tube 212. In the third bottle 206, approximately 1 liter of purified water 220 is sucked into the third bottle 206 to form another 100 times dilution of the homeopathic ingredient solution 218. This dilution process may occur multiple times until a desired dilution of the homeopathic ingredient solution 218 is achieved.

As discussed above, the entire dilution occurs in an environment free of carbon dioxide. For example, argon gas of purity 0.99999 is used. After dilution of six times, or one trillion times weaker, the concentration may reach $10^{-15}$ of the original concentration of the homeopathic ingredient solution 218. At this stage of the dilution process, the homeopathic ingredient solution 218 is considered pure. Consequently, after six successive dilutions, or once the concentration is $10^{-15}$, the original homeopathic ingredient solution 218 can no longer be detected by any current methods, and the homeopathic ingredient solution 218 is considered very pure. At this stage, the homeopathic ingredient solution 218 is in the process of forming into a solid water particle solution 300.

A Step 104 comprises applying an electrical field to the homeopathic ingredient solution 218 and the purified water 220. The electrical field may be applied with a circuitry 214. The circuitry 214 may include, without limitation, a battery, wiring, a voltage, a resistor, and a capacitor. In one embodiment, a wire carrying direct current passes through the homeopathic ingredient solution 218 during the distillation Step 102.

The electrical field aligns the water molecules, such that a large clump 404 of solid water particles forms. This is possible, since the atomic configuration of water is susceptible to orientation from electrical energy and magnetic force. The electrical field may include, without limitation, a direct current electrical field. In some embodiments, an electromagnetic field may also be applied to the homeopathic ingredient solution 218, along with the electrical field.

A Step 106 comprises forming a solid water particle solution 300, the solid water particle solution 300 comprising a large clump 404 of solid water particles. The formation of solid water particles is complete at this Step 106. The solid water particles may include ordinary water containing clumps 404 of solid water particles and simple water molecules.

Those skilled in the art will recognize that these variable water molecules are often called flickering-water-clusters because the hydrogen bonds are broken randomly by thermal energy and then recombine. The present invention deals with clumps 404 and clusters 406a-b of solid water particles that are comprised of a fixed number of water molecules having a steady stable electric field surrounding them. In one possible embodiment, the solid water particles are generally soft and jelly-like. In this configuration, the solid water particles can bend under pressure, unlike an ordinary solid.

Figure 3:
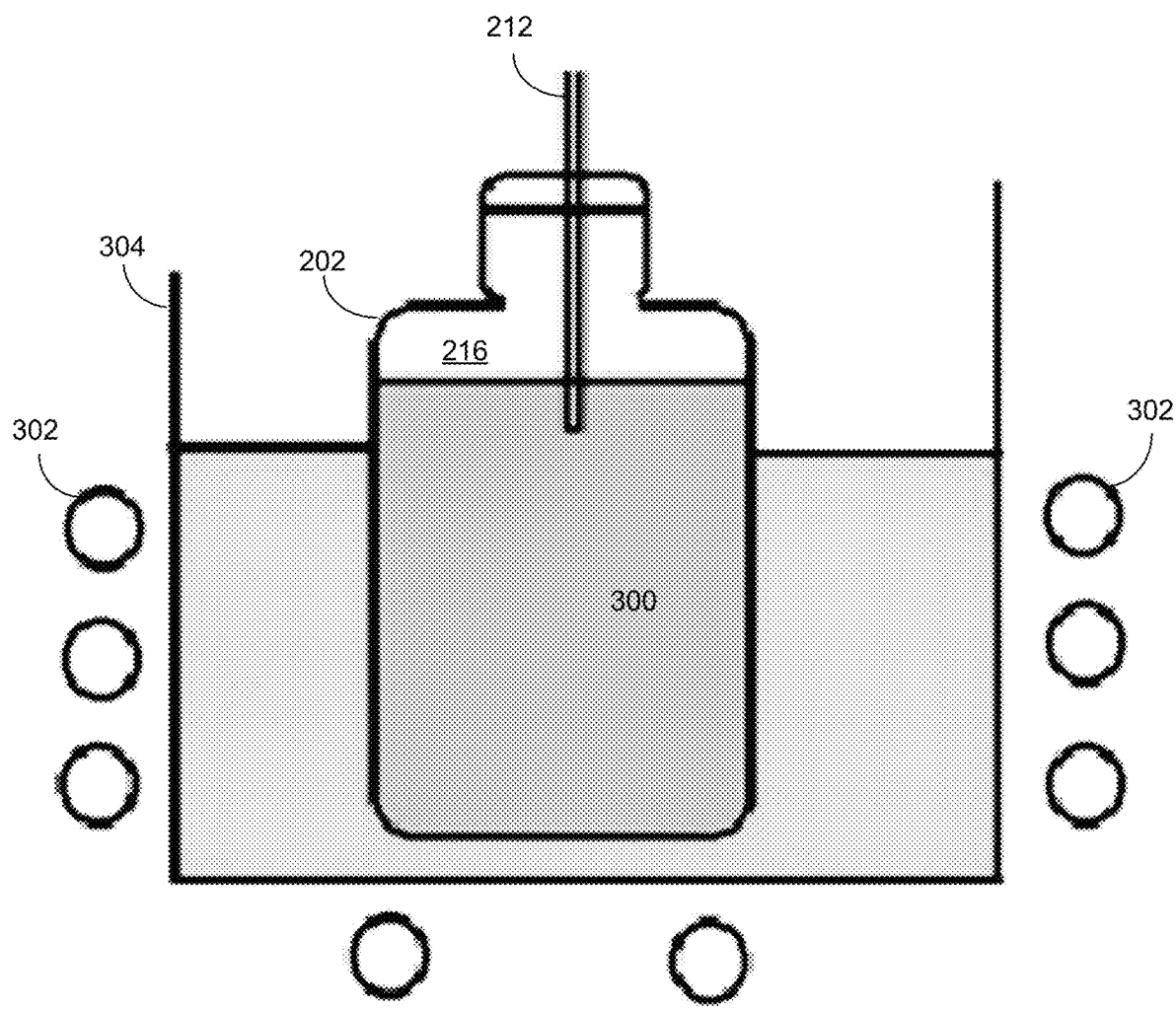
FIG. 3 illustrates an exemplary ultrasonic sonicator disrupting a large clump of solid water particles, in accordance with an embodiment of the present invention.

A Step 108 may include applying, in a water bath 304, an ultrasonic vibration to the solid water particle solution 300. As illustrated in FIG. 3, the solid water particle solution 300 is placed in a water bath 304, where an ultrasound sonicator 302 generates the ultrasonic vibration. The ultrasonic vibration may include vibrations of frequencies greater than the upper limit of the audible range for humans, i.e., greater than about 20 kilohertz. Generally, the high range of vibrations cause cavitation to form in the solid water particle solution 300, which themselves serve to generate vigorous vibrations.

In some embodiments, the ultrasonic vibration may be actuated by mechanical means, including, without limitation, linearly:left and right; forward and backward; up and down; circular rotation: counterclockwise then counter-clockwise. In this manner, a great change of momentum occurs during change of direction either in linear motion or circular motion. It is also significant to note that the step of serial dilution and the step of ultrasonic vibration are performed independently or in alternative series In some embodiments, the vibrations may cause a large clump 404 of solid water particles to form. The vibrations may also break up the large clump 404 into small clusters 406a-b. The large clump 404 forms and breaks; and the small clusters 406a-b grow into new, larger clumps 404, as a result of principles of quantum physics.

For example, using a simple quantum mechanical model. One skilled in the art may assume water molecules are represented by a point-like object with an electric dipole moment $P_o$ and $P_o$=e a, where "e" has the positive value of the charge of an electron, and "a" is the distance between two dipoles 408a, 408b of one water molecule, which is approximately 0.3 nm. A cluster 404, 406a-b of water molecules are represented as points resting on a two dimensional lattice with equal space "a" in both x and y directions.

The interaction energy among water molecules in the water clusters 404, 406a-b is represented by a dipole-dipole 408a-b interaction:

$$U_{ij}=(p_i \cdot p_j - 3 \cdot p_i \cdot n \, p_j \cdot n)/r_{ij}^3(1/4\pi\varepsilon_o),$$

where the bold face means vector quantity, $p_i$, $p_j$ are electric dipole moment of water molecules between water molecules i and water molecules j, n is the unit vector between the two dipoles 408a-b, and $r_{ij}$ is the distance between these two water molecules.

One skilled in the art may also assume that interaction occurs only among nearest neighbors of water molecules. A simple case of a stable water clump 404 that has ten water molecules represented by a point-like dipole lying in a lattice on two rows and each row has five sites with dipoles 408a-b will be considered. The direction of the dipole 408a only points two ways: to the right (+x direction) and to the left (−x direction).

The method 100 may then utilize a Step 110 of disrupting the large clump 404 of the solid water particles, wherein the disruption breaks the large clump 404 into a small clusters 406a-b of the solid water particles. During this Step, the small clusters 406a-b generally absorbs surrounding water molecules, creating further growth of the small clusters 406a-b into additional large clumps 404.

In a first growth embodiment 400 that illustrates growth of solid water particles from water, a row of any number 1 of water molecules with point-like dipole 408a, 408b p point in one direction. The total dipole moment of this cluster 404 of water molecules is 1 $p_o$. There are (1-1) pair interaction. Each pair of dipole-dipole 408a-b, which has the same direction, has interaction energy of $-2$ u. The sum total of all the interaction energy of this cluster U of dipoles 408a-b of one row is $$U = \sum U_{ij} = -(1-1)(2u)$$

where $$u = -e^2/(1/4\pi\varepsilon_o a),$$

$$\approx -2.4 \text{ eV}.$$

For 1=5, U is equal to ($-8$ u).

In another variation of the first growth embodiment 400, one clump 404 with two rows: the first row with 1 dipole 408a pointing x direction, and the second row with the same number 1 dipole 408b pointing the opposite direction-x. The total energy of nearest neighbor is $$U = -1 \cdot u,$$

Figure 4A:
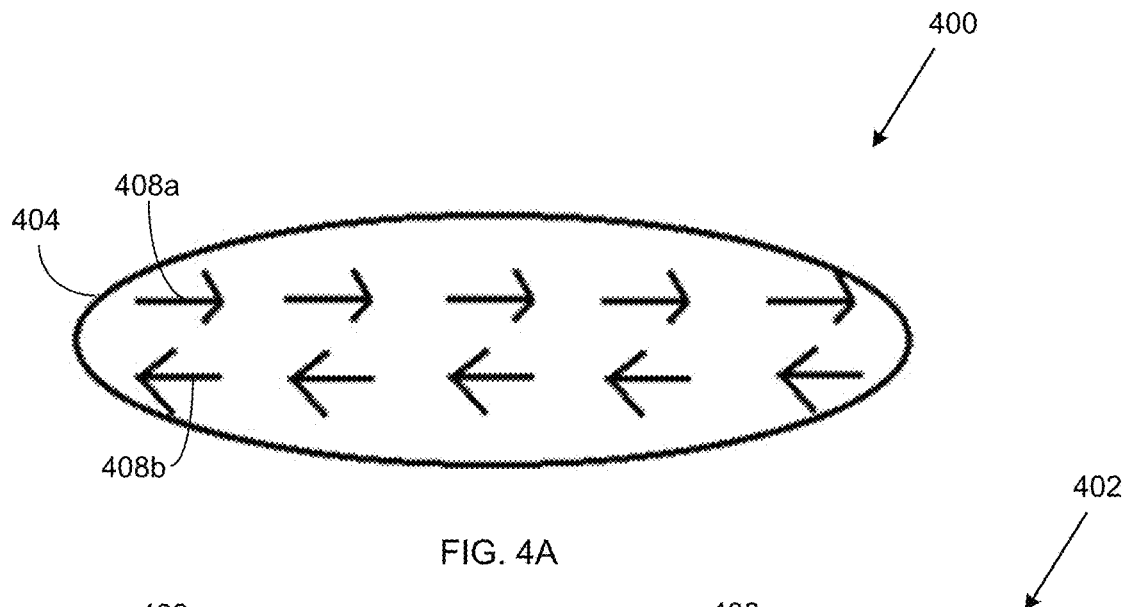
FIGS. 4A, 4B, and 4C illustrate a diagram of an exemplary disruption of a large clump, where

As illustrated in FIG. 4A, a case of clumps 404 with ten molecules with two rows is depicted. Each row has 1=5. That is two rows of five dipoles 408a-b each: in one row, the dipole 408a pointing one way, in the other row, the dipoles 408b are pointing the other way. There are eight pairs of parallel dipoles 408a-b, and five pairs of dipoles 408a-b with dipole 408a pointing in the opposite direction. The two new dipoles 410a, 410b are circled in FIG. 4C. The total energy of the clump 404 is $$U = -8(2u - 5u = -21u.$$

This is the most stable configuration.

Figure 4B:
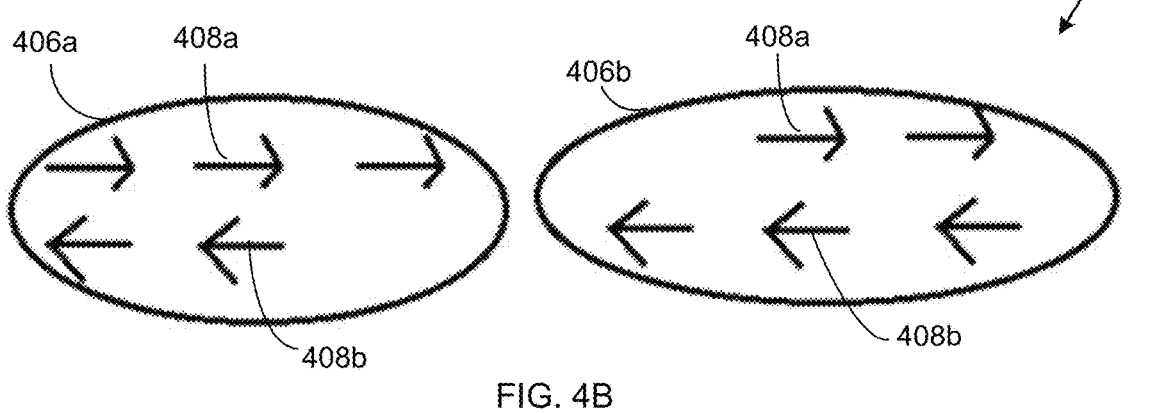
Figure 4C:
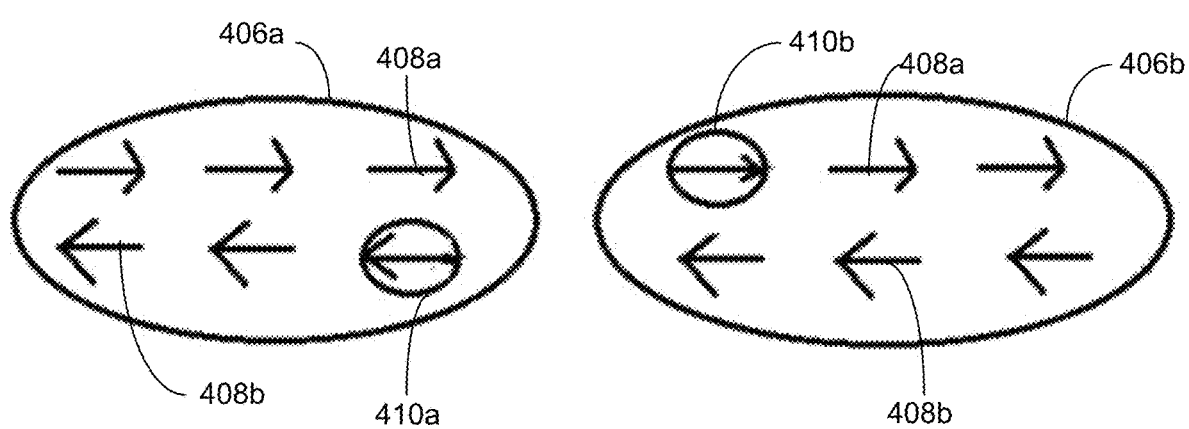

A second growth embodiment 402 illustrates minor vibrational disruption. The big clump 404 of ten molecules may break down into two small clusters 406a-b as shown in FIGS. 4B and 4C. The top row splits into two: one row of three and another of two molecules. The bottom row splits into two: one and four molecules. There are six pairs of dipoles 408a-b with parallel directions, and four pairs with opposite direction. The total energy of these two clusters 406a-b, is U=6($-2$u)+4($-$u)=$-16$ u.

These two clusters 406a-b each can absorb one new water molecules to form more solid water particles. These two larger clusters 406a-b contain 8 pairs of dipoles 408a-b with parallel direction and 6 pairs of opposite direction. The total energy of these two new clusters 406a-b, is U=8($-2$u)$-6$ u=$-22$ u, which is one u lower than the original one cluster 404 with five pairs of coupled dipoles 408a-b. Hence energy wise the bulk water favors to have solid water particles.

Figure 5A:
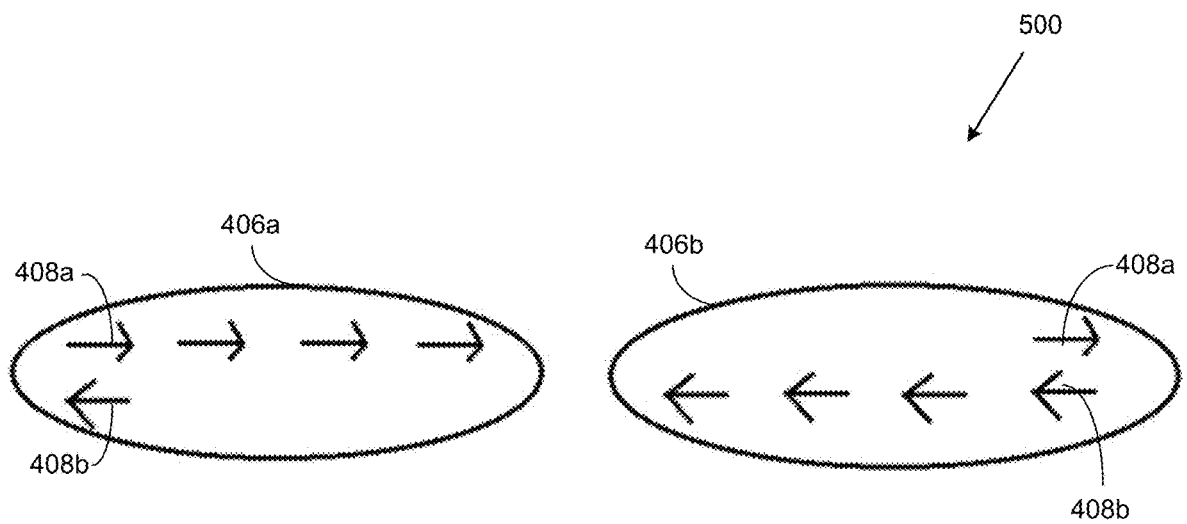
FIGS. 5A and 5B illustrate a diagram of an exemplary disruption of clusters, where
Figure 5B:
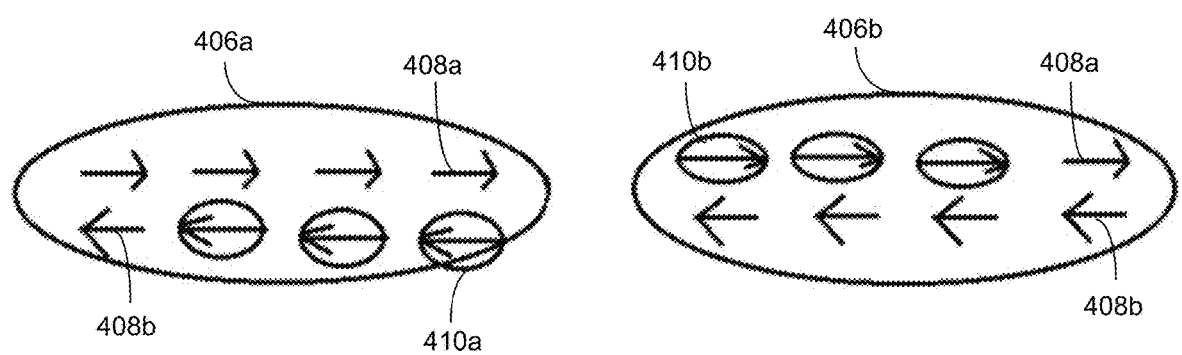
Figure 6A:
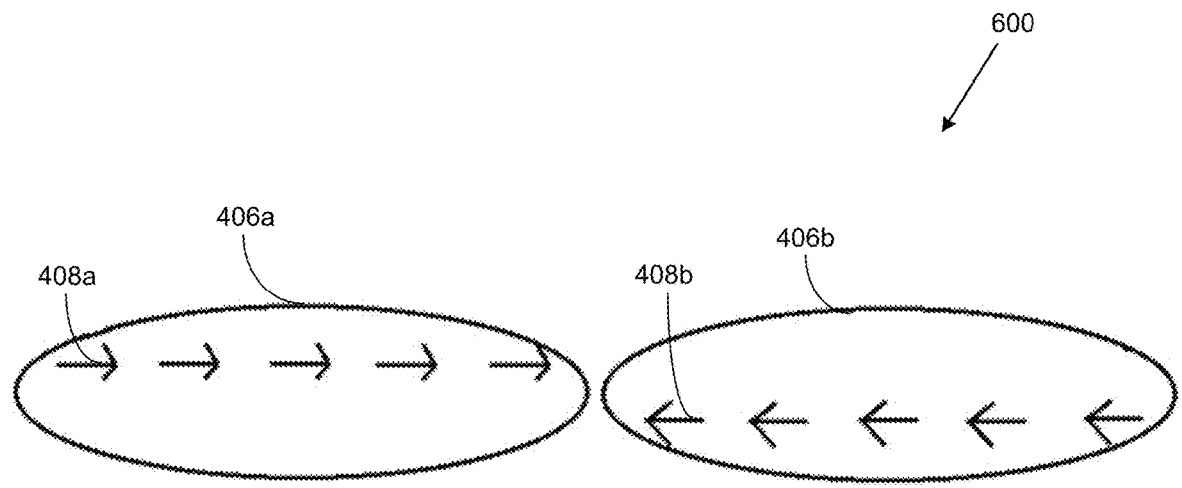
FIGS. 6A and 6B illustrate a diagram of an exemplary disruption of clusters, where
Figure 6B:
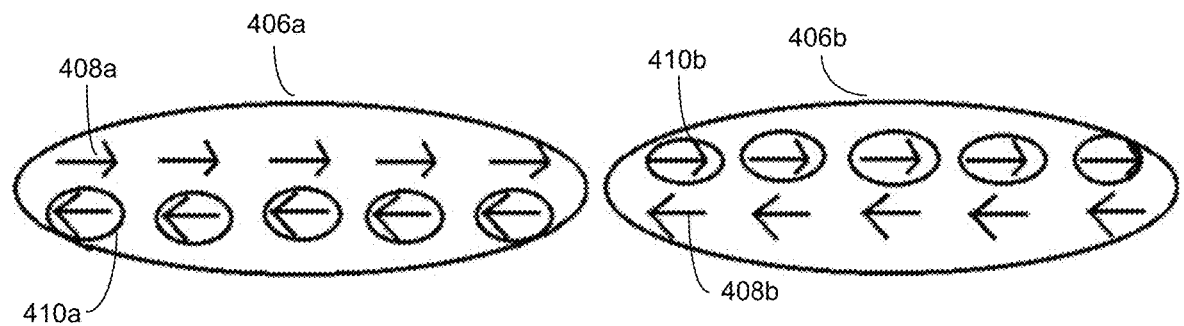

Turning now to FIGS. 5A and 5B, a third growth embodiment 500 addresses major vibrational disruption. Here, some of the larger clusters 406a-b will split into different smaller clusters. The top row splits into 4 and 1 molecules. The bottom row splits into 1 and 4 molecules (FIGS. 5A and 5B). There are six pairs of dipole 408a-b with parallel direction, and two pairs of dipoles with opposite direction. The two new dipoles 410a, 410b are circled in FIG. 5B. The total energy is: U=6 ($-2$ u)$-2$ u=$-14$ u These two clusters 406a-b can absorb three new molecules each. The growth of these two clusters 406a-b represent a gain of six molecules. The total energy of these new clusters 406a-b, each with 8 molecules has 12 pairs of parallel direction and 8 pairs of opposite direction is U=12 ($-2$u)$-8$ u=$-32$ u Looking at FIG. 6A, a fourth growth embodiment 600 addresses circumstances where even great vibrational disruption, such as in ultrasound vibration, occurs. In this example the large clump 404 could split into two small clusters 406a-b. Each cluster 406a-b has only one row, as shown in FIGS. 6A and 6B. The two new dipoles 410a-b are circled in FIG. 6B.

These two one row clusters 406a-b have eight pairs of dipoles 408a-b with parallel direction, and their total energy is $$U = 8(-2upriv) = -16 u$$

They can absorb ten new water molecules in the state of solid water particles to form two larger clusters. These two larger clusters have 16 pairs of dipoles 408a with parallel direction, and 10 pairs of dipoles 408b with opposite direction. The total energy is:

$$U = 2 \times 8(-2 u) - 10 u = -42 u.$$

A Step 112 comprises resting the small clusters 406a-b for a predetermined duration, wherein the inactive period enables the small clusters 406a-b to grow larger than the prior large clump 404 of the solid water particle. Those skilled in the art will recognize that bulk water always wants to go to the lowest energy state, as thermodynamics law dictates. The above example shows that going to lowest state means more growth of the solid water particles. So after vibrating there must be a rest time for the growth of solid water particles. If the vibration is non-stop, solid water particles will grow, but the growth will stop at some equilibrium point. Intervals of vibration and rest, as is done in homeopathic preparation, will grow more solid water particles. It is not necessary as in homeopathy to dilute during the rest period.

In one alternative embodiment, the solid water particle solution 300 is placed in a vacuum for evaporation, and a heater or an infrared lamp heats the solid water particle solution 300, such that a higher concentration of solid water particles occurs. The generated heat actuates growth of the clusters 406a-b A Step 114 further includes repeating the ultrasonic vibration Step 108 and the resting Step 112 until a predetermined concentration of solid water particles forms in the solid water particle solution 300 FIG. 4A). Those skilled in the art will recognize that a continuous cycle of sonic vibrations and rest allow for the maximum growth rate of clusters 406a-b into larger clumps 404 of solid water particles. This results in a solid water particle solution 300 with a higher concentration of solid water particles than can be achieved by just serial dilution alone.

However, as explained above, if the vibration is non-stop, solid water particles will grow, but the growth will stop at some equilibrium point. Intervals of vibration and rest, as is done in homeopathic preparation, will grow more solid water particles. It is not necessary as in homeopathy to dilute during the rest period. Furthermore, the above simple case can also indicate that the more vigorous the vibration, the greater amount of solid water particles is created. Nonetheless, all steps and procedures in the method 100 should be done with purified water 220 and in an environment of inert gas 216 without non-carbon dioxide so as to minimize the amount of charged particles in the environment to influence the growth rate of clusters 406*a-b* into progressively larger, and larger clumps 404 of solid water particles.

A final Step 116 comprises administering the solid water particle solution 300 for therapeutic relief. Because the solid water particle solution 300 is produced through homeopathic means, medical relief is the ideal goal. Myriad diseases and ailments may be addressed through this homeopathic medication. For example, the solid water particle solution 300 is configured to cure, without limitation, an antibacterial, an antivirus, an antifungal, a cure for anti-immune diseases, an alternative method for acupuncture, pain relief, and general relief from various chronic disease syndromes. Furthermore, the solid water particle solution 300 is configured to be administered, without limitation, orally, breathing in via nebulizer, breathing in via vaporizer, intravenously, applied topically on skin as cream, and sprayed on the skin, drops into eyes, ears, noses, anus, or mouth.

Since many modifications, variations, and changes in detail can be made to the described preferred embodiments of the invention, it is intended that all matters in the foregoing description and shown in the accompanying drawings be interpreted as illustrative and not in a limiting sense. Thus, the scope of the invention should be determined by the appended claims and their legal equivalence.

What is claimed is:

1. A method for production of solid water particles for homeopathy, which is used in curing anti-immune diseases, the method comprising:
- performing serial dilution of a homeopathic ingredient solution in purified water;
- applying an electrical field to the homeopathic ingredient solution and the purified water;
- forming a solid water particle solution having a clump of solid water particles;
- applying ultrasonic vibration to the solid water particle solution directly on a container or through a water bath in directions including linear, left and right, forward and backward, up and down, or circular rotation;
- breaking the clump of the solid water particles into a cluster of the solid water particles by the ultrasonic vibration;
- resting the cluster of the solid water particles for absorbing water molecules to increase the amount of the solid water particles;
- repeating the ultrasonic vibration step and the resting step to concentrate the solid water particle solution having the solid water particles with a concentration of one thousandth of one mole;
- placing the solid water particles in a vacuum until water evaporates from the solid water particle solution;
- placing the solid water particles under a heater until water evaporates from the solid water particle solution.

2. The method of claim 1, wherein the purified water has a resistivity of 18.2 Mohm/cm, and pH value of 7.

3. The method of claim 1, wherein the step of performing serial dilution is performed in an inert gas, the inert gas is Argon or Nitrogen.

4. The method of claim 1, wherein the ultrasonic vibration is formed by an ultrasound sonicator.

5. The method of claim 1, wherein the step of serial dilution and the step of ultrasonic vibration are operable independently or in alternative series.

6. The method of claim 1, wherein the step of serial dilution and the step of ultrasonic vibration are operable under the electrical field.

7. The method of claim 1, wherein the step of serial dilution and the step of ultrasonic vibration are operable under an electromagnetic field.

8. The method of claim 7, wherein the step of serial dilution and the step electromagnetic field.

9. The method of claim 1, wherein the step of ultrasonic vibration is performed intermittently with a short duration of rest time between vibrations.

10. The method of claim 1, wherein the solid water particles are generally soft and jelly-like, the solid water particles are configured to bend under pressure.

11. The method of claim 1, wherein the method forms solid water particles in accordance to the principles of quantum mechanics.

12. The method of claim 1, further including the step of placing the solid water particle solution in a vacuum for evaporation, wherein a heater or an infrared lamp heats the solid water particle solution, wherein the heat actuates a higher concentration of solid water particles.

13. A method for production of solid water particles for homeopathy, which is used in curing anti-immune diseases, the method comprising:
- performing serial dilution of a homeopathic ingredient solution in purified applying an electrical field to the homeopathic ingredient solution and the purified water;
- forming a solid water particle solution having a clump of solid water particles;
- applying ultrasonic vibration to the solid water particle solution directly a container or through a water bath in directions including linear, left and right, forward and backward, up and down, or circular rotation;
- breaking the clump of the solid water particles into a cluster of the solid water particles by the ultrasonic vibration;
- resting the cluster of the solid water particles for absorbing water molecules to increase the amount of the solid water particles;
- repeating the ultrasonic vibration step and the resting step to concentrate the solid water particle solution having the solid water particles with a concentration of one thousandth of one mole;
- placing the solid water particle solution in a vacuum for evaporation;
- heating the water particle solution with a heater or an infrared lamp, wherein the heat actuates the formation of a higher concentration of solid water particles.

14. The method of claim 13, wherein the purified water has a resistivity of 18.2 Mohm/cm, and pH value of 7.

15. The method of claim 13, wherein the step of performing serial dilution is performed in an inert gas, the inert gas is Argon or Nitrogen.

16. The method of claim 13, wherein the step of serial dilution and the step of ultrasonic vibration are operable under the electrical field and the electromagnetic field.

* * * * *